(12) United States Patent
Majidi

(10) Patent No.: US 10,828,134 B1
(45) Date of Patent: Nov. 10, 2020

(54) DENTAL IMPLANT PROSTHETIC AND SURGICAL LIFE-SAVING KIT

(71) Applicant: Amirhossein Majidi, Tehran (IR)

(72) Inventor: Amirhossein Majidi, Tehran (IR)

(*) Notice: Subject to any disclaimer, the term of this patent is extended or adjusted under 35 U.S.C. 154(b) by 0 days.

(21) Appl. No.: 16/699,065

(22) Filed: Nov. 28, 2019

(51) Int. Cl.
*A61C 8/00* (2006.01)
*B25B 13/48* (2006.01)

(52) U.S. Cl.
CPC .......... *A61C 8/0089* (2013.01); *A61C 8/0066* (2013.01); *A61C 8/0068* (2013.01); *B25B 13/48* (2013.01)

(58) Field of Classification Search
CPC ..... A61C 8/0066; A61C 8/0089; B25B 13/48; B25B 13/50
See application file for complete search history.

(56) References Cited

U.S. PATENT DOCUMENTS

| | | | | | |
|---|---|---|---|---|---|
| 4,873,899 | A | * | 10/1989 | Mazurek | B25B 13/463 81/63 |
| 5,290,171 | A | * | 3/1994 | Daftary | B25B 9/00 433/141 |
| 5,727,942 | A | * | 3/1998 | Hartmann | A61C 8/0075 433/141 |
| 5,743,158 | A | * | 4/1998 | Perkins | B25B 13/28 81/58.5 |
| 6,007,336 | A | * | 12/1999 | Sapkos | A61C 8/005 433/141 |
| 6,095,816 | A | * | 8/2000 | Krueger | A61C 8/0087 433/163 |
| 6,162,053 | A | * | 12/2000 | Hollander | A61C 8/0089 433/141 |
| 6,315,562 | B1 | * | 11/2001 | Kumar | A61C 8/0087 433/141 |
| 9,492,249 | B1 | * | 11/2016 | Lefman | A61C 8/0089 |
| 10,420,632 | B2 | * | 9/2019 | Vergoullis | A61C 3/04 |

* cited by examiner

*Primary Examiner* — Ralph A Lewis
(74) *Attorney, Agent, or Firm* — Nasser Ashgriz; UIPatent Inc.

(57) ABSTRACT

The present invention is a dental implant tool comprising of a handle and a head portion connected to each other via a hinge facilitating the head to pivot relative to the handle to enable the dentist to reach various positions within a patient's mouth. The head portion configured to retain an abutment, an impression coping or healing abutment during a dental procedure and can be moved to the left and the right up to 90 degrees. The head comprises a rotatable ratchet with a key-shape center hole to hold an abutment in place while affixing the abutment to an implant and provides a complete access to implant-driver tip to the screw head, regarding to any abutment-body angulation, position and screw access hole. The inner wall of the center hole has 3°-degree convergences at any plan of the walls in order to grasp, lock and hold implant abutments. The dental tool provides practitioners with a better and more enhanced access to the sites of the implants without any limitations, regarding to the implant while minimizing the amount of health risk exposure through increasing the level of safety standards.

10 Claims, 22 Drawing Sheets

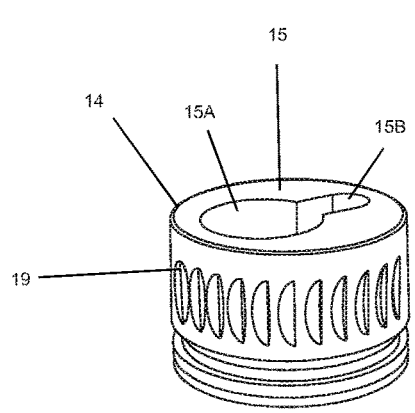
FIG. 3A
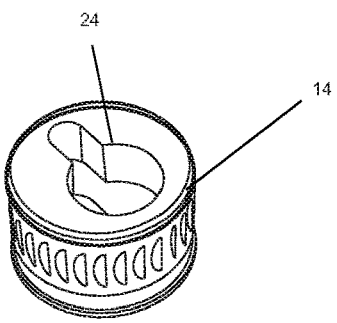
FIG. 3B
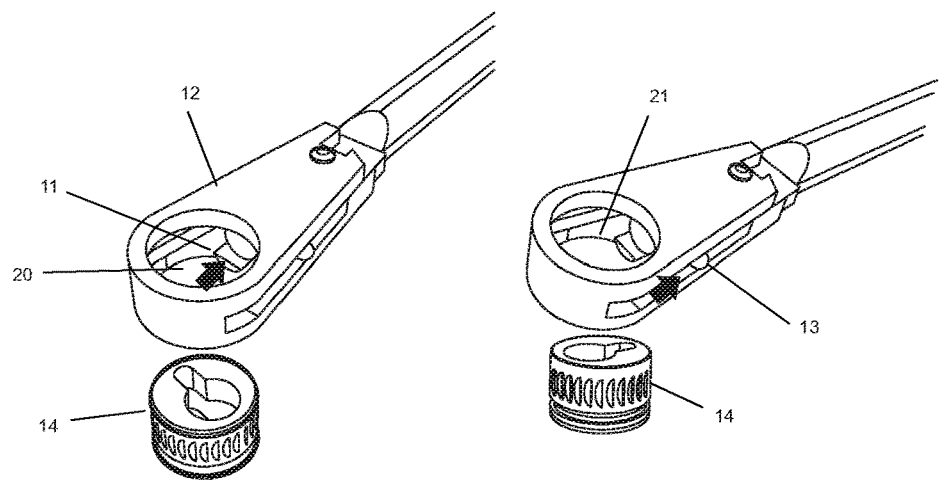
FIG. 4A
FIG. 4B
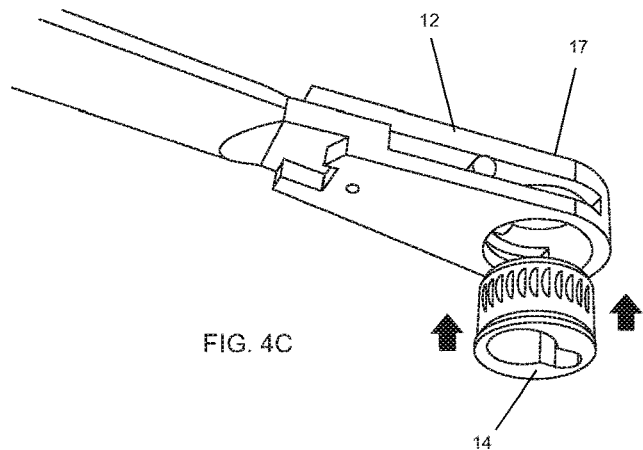
FIG. 4C

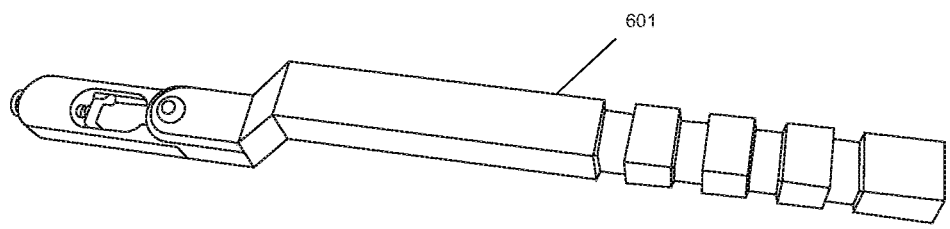
FIG. 24A
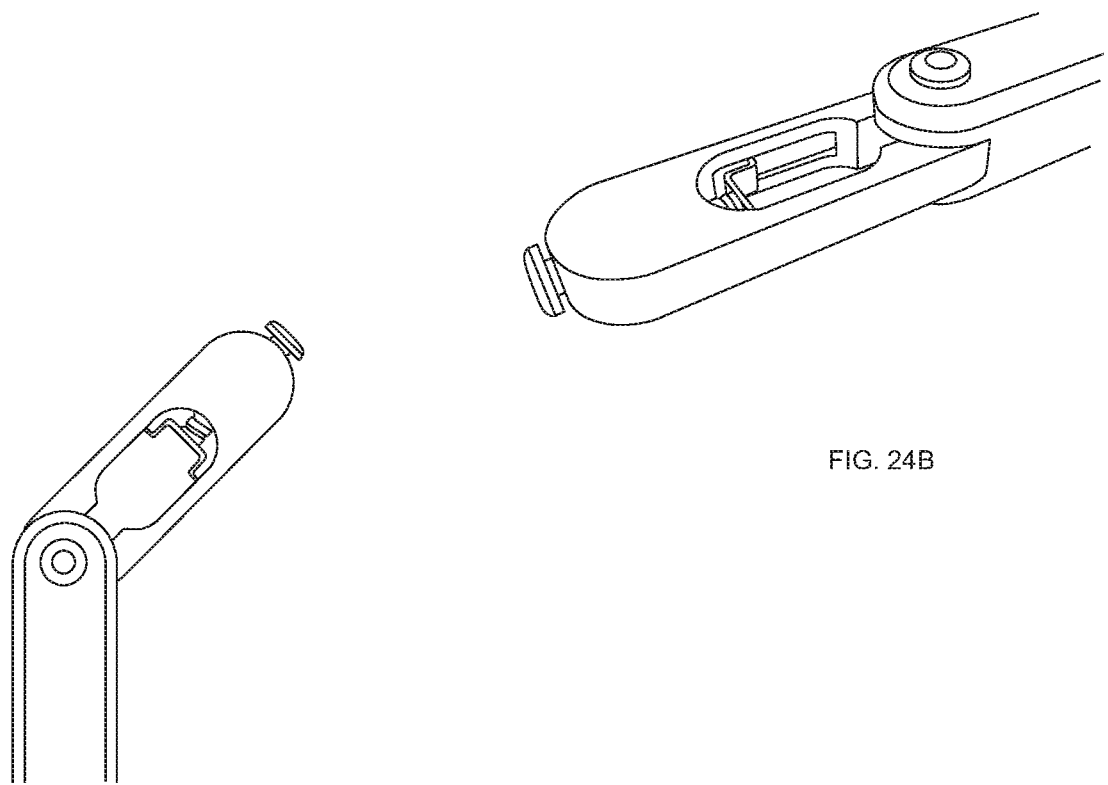
FIG. 24B
FIG. 24C

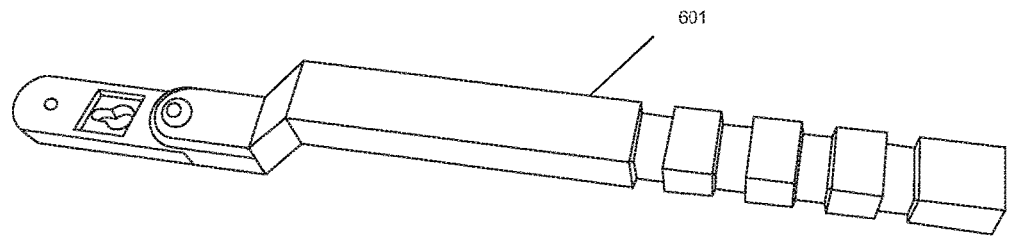
FIG. 25A
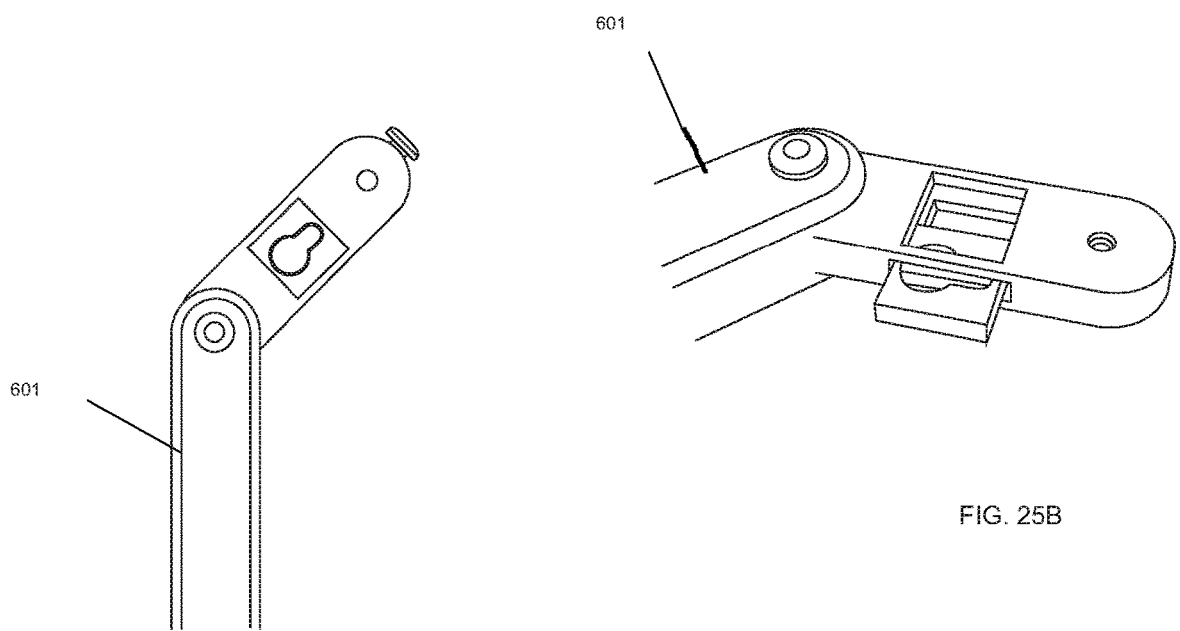
FIG. 25B
FIG. 25C

DENTAL IMPLANT PROSTHETIC AND SURGICAL LIFE-SAVING KIT

FIELD OF THE INVENTION

The present invention relates in general to the field of implant dentistry and in more particular to a set of instruments which includes features that should provide an improvement to the underlying procedure in the implant dentistry as well as matters pertaining to patient safety.

BACKGROUND OF THE INVENTION

Dental implants have been widely used for single-tooth replacements up to full-arch rehabilitations. The long-term predictability of Osseo-integrated oral implants is well documented. A dental implant system consists of an implant that is surgically implanted in maxilla or mandible (upper or lower jaw), and an abutment that mates with the implant once the implant successfully Osseo-integrates to the bone. Depending on the specific system used, an abutment can include a machined connection mechanism within itself or can be clamped onto the implant by means of an abutment screw. The dental prosthesis is then fabricated over the abutment.

To perform this procedure there are many small parts/particles e.g. healing abutments, impression coping and abutments to fix the implant and its components. During dental-implant procedure, those small parts may fall into patient's mouth or throat. This is a common incidence due to the small size of the parts, slippery and lubricated environment by saliva and unwanted movement of patient's tongue.

The fallen objects may pass through two routes; either through food passage or air way passage. Ingestion of artificial crowns and small implant particles such as abutments, impression coping, healing abutment and screwdriver accounts for major share of accidental swallowing by patients. This may result in serious complications such as intestinal perforation. Aspiration of foreign bodies during dental treatment is considered as medical emergency that requires prompt removal. It could create serious life-threatening complications. In this case, Bronchoscopy examination will be done using flexible cable under conscious sedation. Then, micro forceps must be used to remove the object. It is the responsibility of the dentist to see that none of the working parts and instruments fall, especially when the working site is at the posterior teeth.

The existing literature describes mainly the options available for treating the ingestion of sharp and blunt objects during routine dental procedures, but it does not include the prevention of swallowing or aspiration of components used during dental implant placement. As far as the different dental implant components are concerned, it only elaborates on how to secure an implant hex driver, by using dental floss, has been described.

To prevent such accidental complications, ingestion/aspiration, the prevailing standard practice guidelines need to be followed. The guidelines are, however, confined to the use of gauze throat screens or floss ligatures. But, that is not enough. The practitioners ought to be enabled to take some preventative measures in the form of using some instruments to protect their components from being swallowed or aspirated accidentally, offering extra comfort and assurance to the dentists while resulting in a higher and better standard protection for the patients.

Moreover, dental implants are not implanted exactly parallel to adjacent teeth roots normally, based on:
Surgical limitations such as: Bone topography, Anatomical landmarks, Bone resorption;
Prosthetic considerations: Occlusion issues, Dental space analyzing, specified prosthetic treatment plans;
The innate nature of manual surgical procedures, the surgeon does not have an accurate and precise way to locate the adjacent roots, and
Sometimes because of lack of experience and accuracy.

While the implant is not parallel to Occlusal plan based on the above-mentioned criteria, the abutment should be parallel to adjacent teeth-long axes and perpendicular to occlusal plan, for restorative purposes and to adhere to prosthetics fundamentals, therefore as the screw of the abutment is being placed and tighten parallel to the long axes of the implant, the access-hole to the abutment screw head inside the body of the abutment, would not be at very top of the abutment (the shape of implant abutment is like cone-frustum) in most cases.

In this manner, conventional lock-in grasping tools in dentistry, such as needle-holders, hemostats, forceps, are not practically useful by blocking the access-hole of the abutment to the screw-head (located on sides of abutment cone) to grasp the components.

To overcome the above-mentioned problems, the present invention provides a special "Dental Implant Prosthetic and surgical life-saving kit" to assist the dentist to establish and maintain a firm grasp over the components during transfer from working cast to the patient's mouth and vice versa.

SUMMARY OF THE INVENTION

In a preferred embodiment, the present invention is a dental tool for installing a dental abutment. The dental tool is an implant prosthetic and surgical holder to hold the dental implant components during the implant procedure and provide safety standards to eliminate hazards of complications resulting from ingestion of small objects.

The dental tool comprises of a handle that connects to a head portion by a hinge. The head portion of the dental tool configured to selectively retain an abutment, impression coping, or a healing abutment, during a dental procedure and can pivot relative to the handle to enable the dentist to reach various positions within a patient's mouth. It can be extended up to 90 degrees at each direction (180° range). Rotational head makes it usable on any part of the jaws and cover all clinical implant position and angulation possibilities.

The head comprises an aperture to receive a ring-shaped ratchet with a center hole to hold an abutment in place while affixing the abutment to an implant. The center hole of the ratchet has a Key-Hole design, that provides a complete approach and access to implant-driver tip to the screw head, regarding to any abutment-body angulation, position and screw access hole. The inner walls of the key-hole have 3°-degree convergences at any plan of the walls in order to grasp, lock and hold implant abutments which have cone-frustum designs with 2°-3° convergences in each wall.

The abutment, impression coping, or healing abutment is being inserted into the key-hole of the dental tool and can be positioned in place to fasten the abutment into an implant by a screwdriver. Once positioned over the implant, the dentist can hold the dental tool to adjust the position of the abutment on the implant and thread the screw into the implant. Once the abutment or other components are secured to the implant, the dental tool 100 can be released and removed from the mouth of the patient.

The head portion of the dental tool provide a locking mechanism to adjustably hold the ratchet inside the aperture. The ratchet has grip retaining gaps extended continuously around the outer side wall thereof in communication with a catch portion of the aperture to be rotatably and firmly grasp the ratchet. Once the abutment or other components are inserted within the dental tool; the dentist can transport the abutment or other components to the desired location within a patient mouth to affix the abutment or other components to an implant.

Additionally, or alternatively, the handle can be in various shapes to aid the dentist in placing the dental tool within the oral cavity. The handle can be straight, curved, or have a combination of straight sections and curved sections.

In another embodiment, the present dental tool comprises of a handle having two hinges on its proximal end to receive two heads to enable the practitioner to transfer two abutments or other components at the same time.

The present invention can be produced as a kit of a complementary set of tools to all dental implant procedures, especially prosthetic treatment and this kit can provide the various shape of handles and head portions to prevent major life-threatening hazards.

It is therefore an object of the present invention to provide a dental tool for safe insertion and extrusion of components which eliminates hazards such as reduction or elimination of complications resulting from ingestion or aspiration of small objects.

It is further another object of the present invention to provide a dental tool that can be used for all implant brands in the market and even to all forms and shapes of abutments, either prefabricated or customized types.

It is another object of the present invention to provide a better vision for the practitioner during the implant procedure.

It is another object of the present invention to provide a dental tool for holding the dental components in correct position during screwing down and unscrewing.

It is another object of the present invention to eliminating risk of components and small parts from falling on the ground that most often result in disruption of patient's treatment.

It is another object of the present invention to saves a great deal of time by providing a faster and safer technique, which allows the transferring of implant-components in and out of the mouth cavity, thereby saving costs for the patients as well as a higher return for the dentist.

It is another object of the present invention to create a better opportunity for the dental practitioner to make it easier to prevent the complications normally associated with such a procedure. These complications include the accidental swallowing or aspiration of the components of the dental implant.

It is another object of the present invention to provide a Key-Hole design to hold the abutment in the implant process, that provides a complete approach and access to implant-driver tip to the screw head, regarding to any abutment-body angulation, position and screw access.

It is another object of the present invention to provide a rotational head that can be extended up to 90 degrees in each direction (180 range) which makes it practical at any part of the jaws and cover all clinical implant position and angulation possibilities.

BRIEF DESCRIPTION OF THE DRAWINGS

Embodiments herein will hereinafter be described in conjunction with the appended drawings provided to illustrate and not to limit the scope of the claims, wherein like designations denote like elements, and in which:

FIG. 3A is a perspective view of the ratchet of the head portion;

FIG. 3B is a perspective top view of the ratchet of the head portion;

FIG. 4A is a perspective view of the head portion showing the insertion of the ring into the aperture of the head portion;

FIG. 4B is a perspective view of the head portion showing the insertion of the ring into the aperture of the head portion;

FIG. 4C is a perspective view of the head portion showing the insertion of the ring into the aperture of the head portion;

FIG. 24A is a perspective view of another embodiment of the present invention;

FIG. 24B is a perspective view of the head portion according to FIG. 24A;

FIG. 24C is a perspective view of the head portion according to FIG. 24A;

FIG. 25A is a perspective view of another embodiment of the present invention;

FIG. 25B is a perspective view of the head portion according to FIG. 25A;

FIG. 25C is a perspective view of the head portion according to FIG. 25A;

DETAILED DESCRIPTION OF PREFERRED EMBODIMENTS

Figure 1:
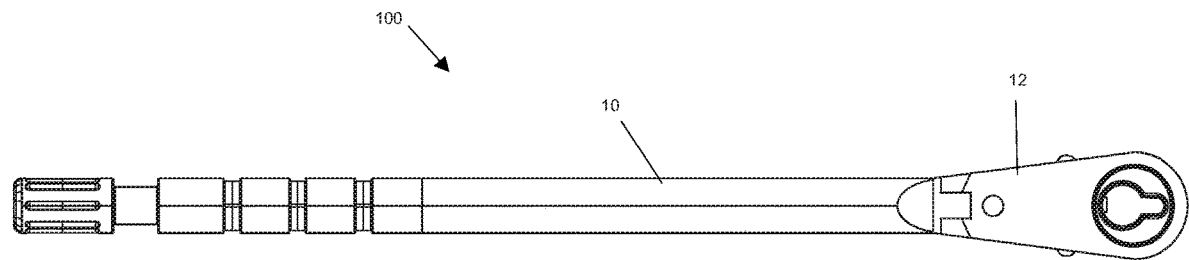
FIG. 1 is a perspective view of the dental implant prosthetic and surgical tool.
Figure 2:
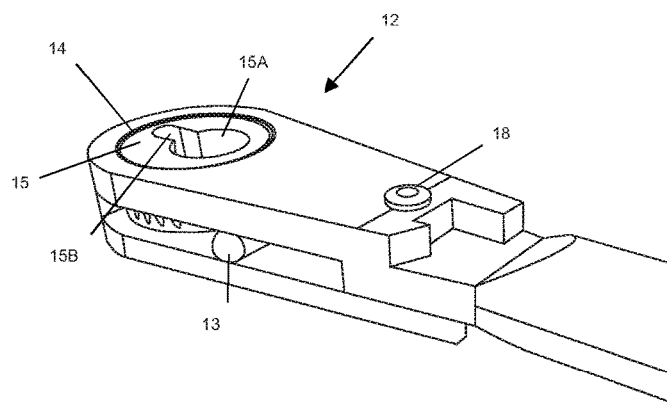
FIG. 2 is a perspective view of the head portion of the dental tool.

FIGS. 1 to 9 show the first embodiment of the present dental implant prosthetic holder 100 comprising of a handle 10 that connects to a head portion 12 via a hinge. The handle 10 is pivotally connected to the head portion 12 from the proximal end at a pivot point 18. The head portion 12 of the dental tool 100 configured to hold an abutment during a dental procedure and can be moved to the left side and the right side and be secured at each direction. It can be extended up to 90 degrees at each direction (180° range) which is one of the key features of the present invention.

According to FIGS. 4A and 4B, the head 12 comprises of an aperture 20 with a circular inner side wall 21 adapted to receive a cylindrical ring shape ratchet 14. A locking mechanism is provided on the head portion 12 to rotatably fix and hold the ratchet 14 inside the aperture 20. The ratchet 14 has a key-shape-hole 15 in the centre comprising of a circular section 15a and a stem section 15b adapted to hold an abutment 30 in place while affixing the abutment 30 to an implant 40. The key-hole 15 has an inner side wall 24 with 3 degree convergences from the upper surface towards the lower surface of the ratchet 14 in order to grasp, lock and hold implant abutment 30 which have cone-frustum designs with 2°-3° convergences in each wall. This structure of the key-hole 15 enables to insert and grip a variety of different sized abutments 30 in the key-hole 15.

As shown in FIGS. 3A and 3B, the key-hole 15 design, provides a complete approach and access to implant-driver tip to the screw head, regarding to any abutment-body angulation, position and screw access hole. The screw head can access through the stem section 15b of the key-hole 15 to the implant-driver tip while the implant abutment 30 is securely placed into the circular section 15a of the key-hole 15.

Again, as shown in FIGS. 3A, 4A-4C, a locking mechanism is provided to moveably fix the rachet 14 inside the aperture 20 and prevent extra movement of the rachet 14 after fixation of the abutment 30. The inner side wall 21 of the aperture 20 has a moveable catch mechanism which moves forward and backward in a groove 17 provided on the sides of the head portion 12. The catch mechanism comprises a knob 11 slidably movable by a lever 13 in communication with the grip retaining gaps 19 extended continuously around the outer side wall of the rachet 14 to rotatably and firmly grasp the ratchet 14.

Figure 5A:
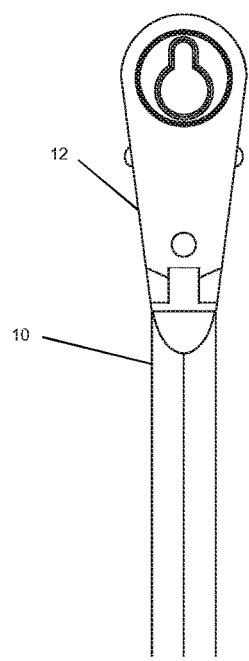
FIG. 5A is a front view of the dental tool showing the handle pivotable with respect to the head portion to the right.
Figure 5B:
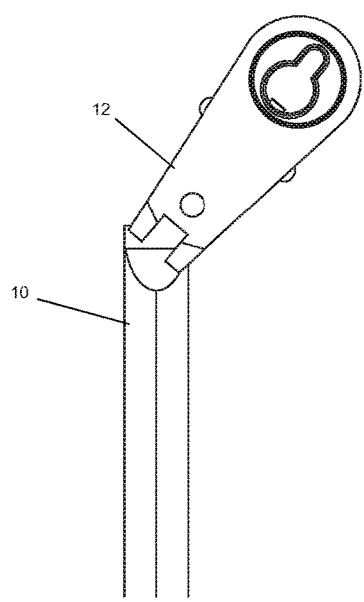
FIG. 5B is a front view of the dental tool showing the handle pivotable with respect to the head portion to the right and extended to 90 degrees.
Figure 5C:
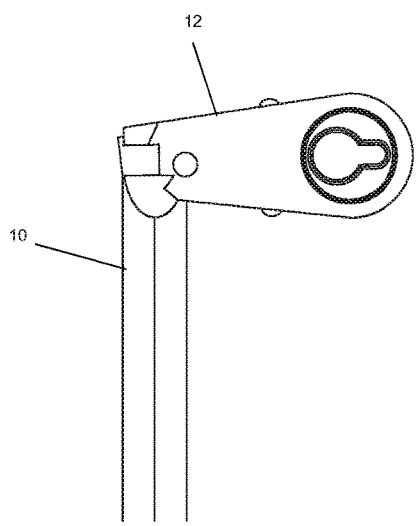
FIG. 5C is a front view of the dental tool showing the handle pivotable with respect to the head portion to the right and extended to 90 degrees.

As shown in FIGS. 5A-5C, the head 12 is pivotably connected to the handle 10 to selectively pivot between an upright position (FIG. 5A) to an angled position (FIG. 5B) and to a perpendicular position (FIG. 5C) to enable the dentist to reach various positions within a patient's mouth. Alternatively, the handle 10 can be in various shapes to aid the dentist in placing the dental tool 100 within the oral cavity. The head 12 can be angled various axis relative to the handle 10. This angled arrangement can generally aid in the placement of the dental tool 100 within a patient's mouth and proximate to a work site. Furthermore, the head 12 can pivot, rotate, or move relative to the handle 10.

Figure 6:
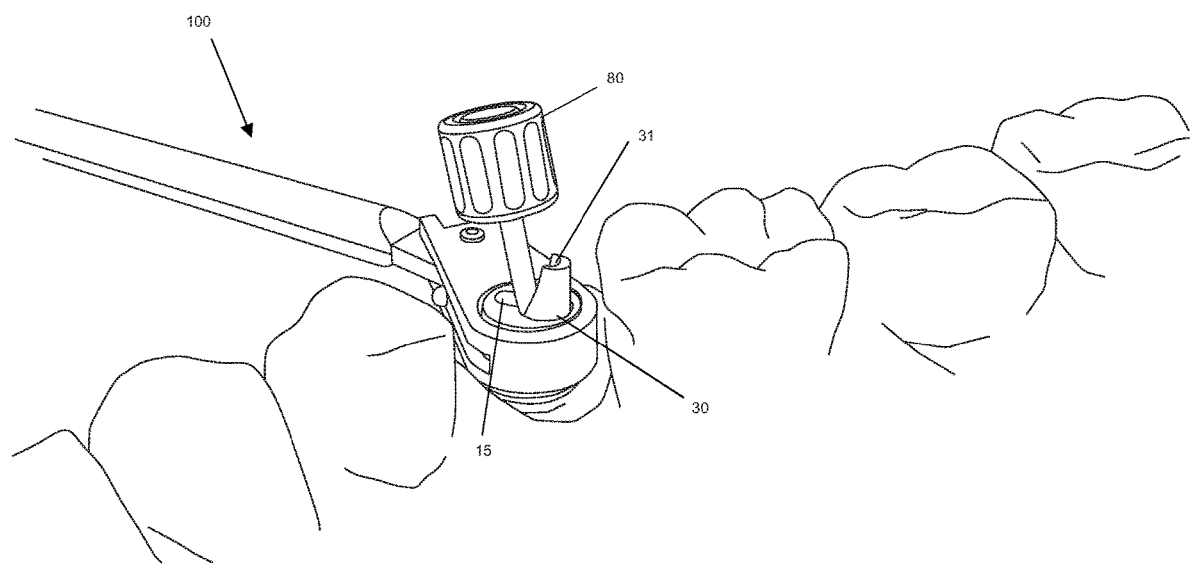
FIG. 6 is a perspective view depicting the dental tool adjustably grasping an abutment for assistance in the driving of the screw into an implant.
Figure 7A:
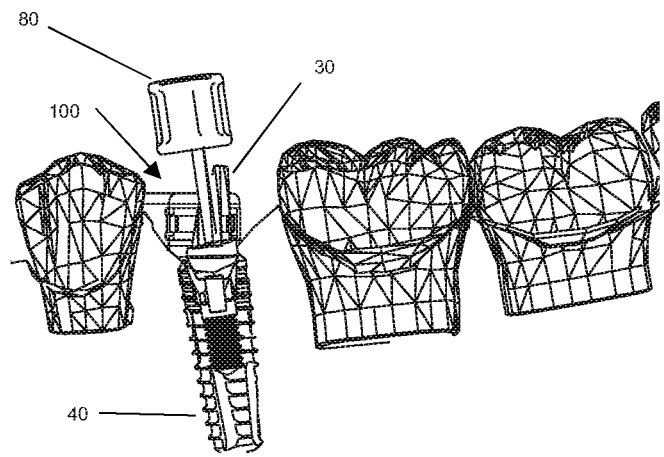
FIG. 7A is a cross sectional view of the present invention adjustably grasping an abutment for assistance in the driving of the screw into an implant.
Figure 7B:
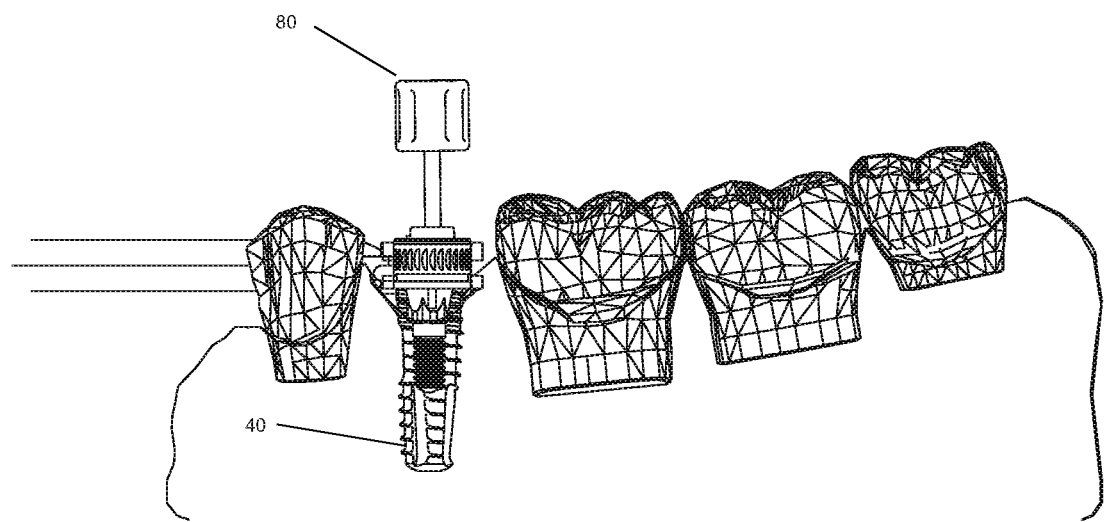
FIG. 7B is a cross sectional view of the present invention for assistance in the driving of the screw into an implant.
Figure 8:
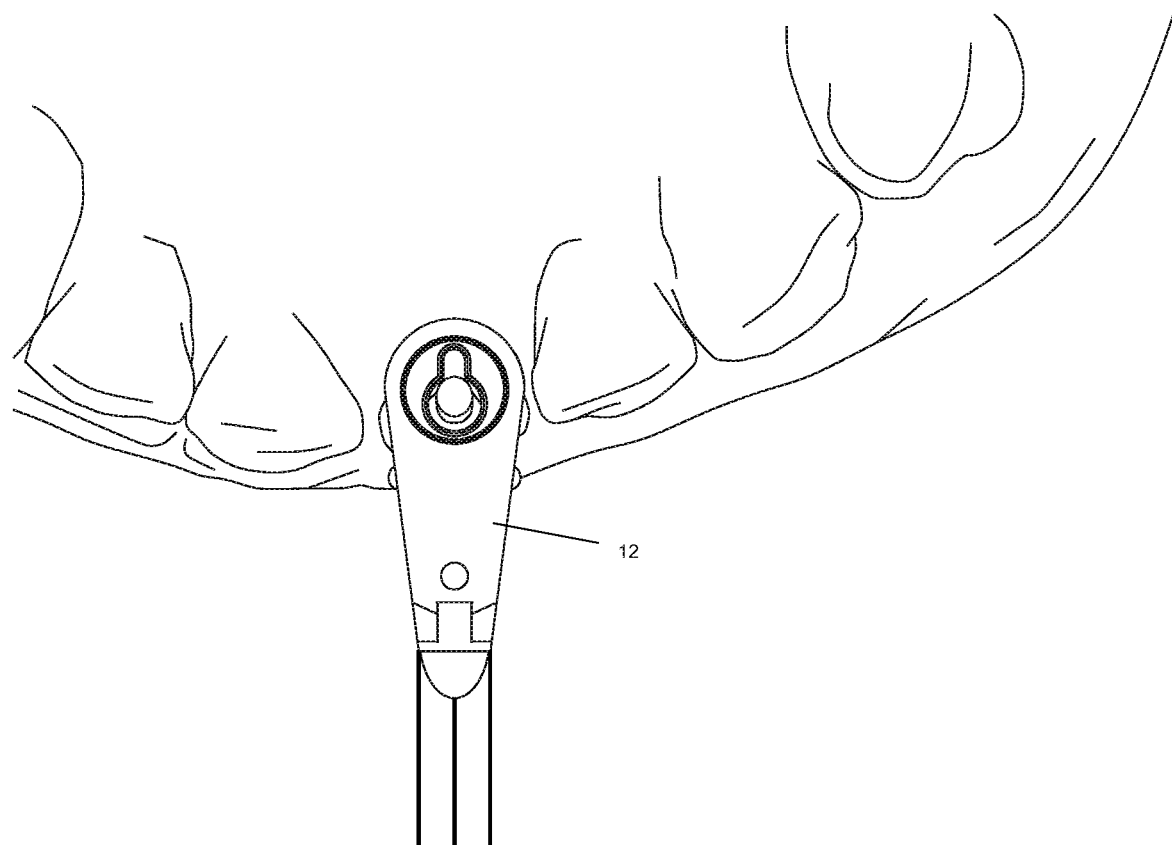
FIG. 8 is a top view showing the present invention adjustably grasping an abutment for assistance in implant procedure.
Figure 9:
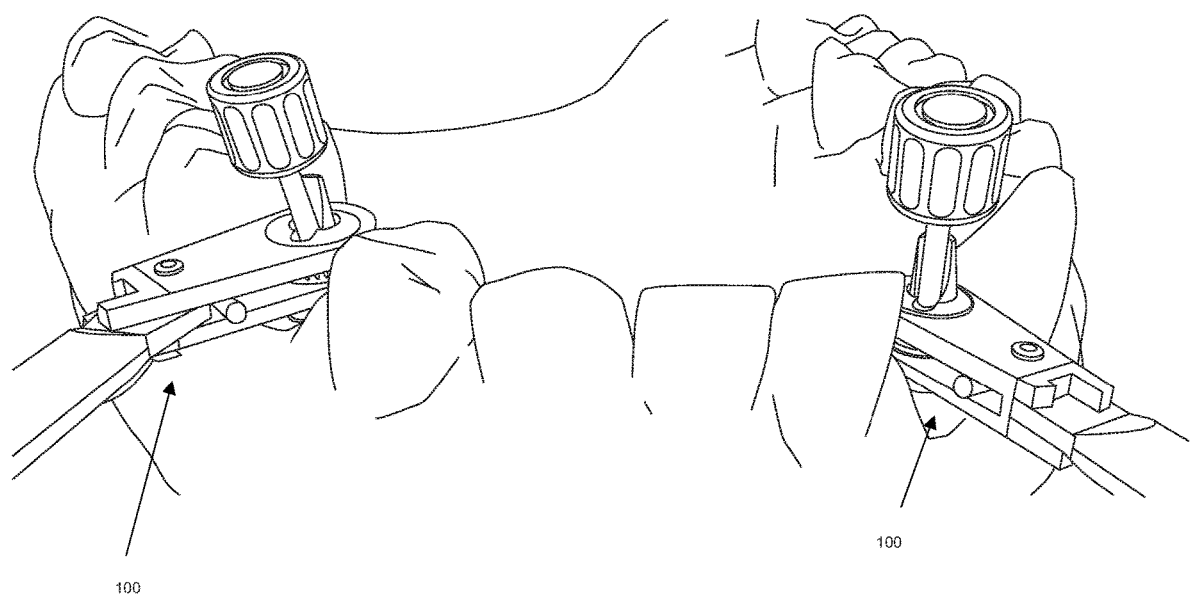
FIG. 9 shows the present invention used for 2 implant sites of a patient.

FIGS. 6 to 9 show the dental tool 100 during the operation. As shown in FIG. 6, the abutment 30 is inserted into the key-hole 15 and being held within the key-hole 15. Once the abutment 30 is engaged within the dental tool 100 the dentist can transport the abutment 30 to the desired location within a patients mouth to affix the abutment 30 to an implant 40. Generally abutments 30 have a hole 31 in which an adjusting screw 80 can be inserted to fasten the abutment 30 onto the implant 40. Once positioned over the implant 40, the dentist can hold the dental tool 100 to adjust the position of the abutment 30 on the implant 40. The key-shape structure provides a space for the screw 80 to fix the abutment 30. The screw head can access through the stem section 15b of the key-hole 15 to the implant-driver tip while the implant abutment 30 is securely placed into the circular section 15a of the key-hole 15. Once the abutment 30 is secured to the implant 40, the dental tool 100 can be released and removed from the mouth.

The head 12 can be in various shapes and sizes such that it can easily be placed within the oral cavity. The dimension of the head 12 can vary in various shape of the heads but it is desirable to have a length about 1 to-1.5 cm and a width about 4.5 mm or 6.5 mm. The handle 10 can be generally straight, curved, or have a combination of straight sections and curved sections. In some embodiments, the handle 10 has a length in the range of about 5 cm to about 7 cm.

The head portion 12 and the handle 10 are made from the same material. Any suitable material can be used. In some embodiments, the head portion 12 and the handle 10 can be made from medical titanium alloy or stainless steel. In some embodiments, portions of the dental tool 100, such as the entire head 12 or components of the head can be replaceable. In some embodiments, the entire tool 100, or portions thereof, can be sterilized (i.e. via autoclaving) or disinfected in between uses. In some embodiments the dental tool 100 is provided as a "dental tool kit" comprising a plurality of replaceable and/or interchangeable components.

Figure 10:
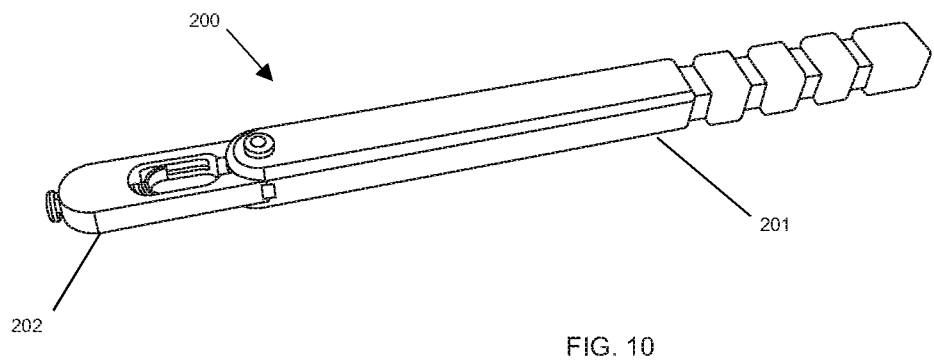
FIG. 10 is a perspective view of anther embodiment of the present invention.
Figure 11:
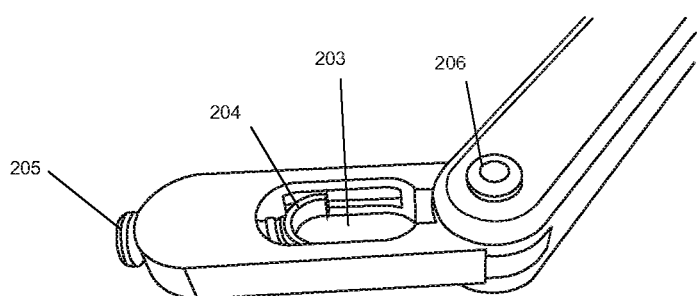
FIG. 11 shows the head portion of the present invention according to FIG. 10.
Figure 12:
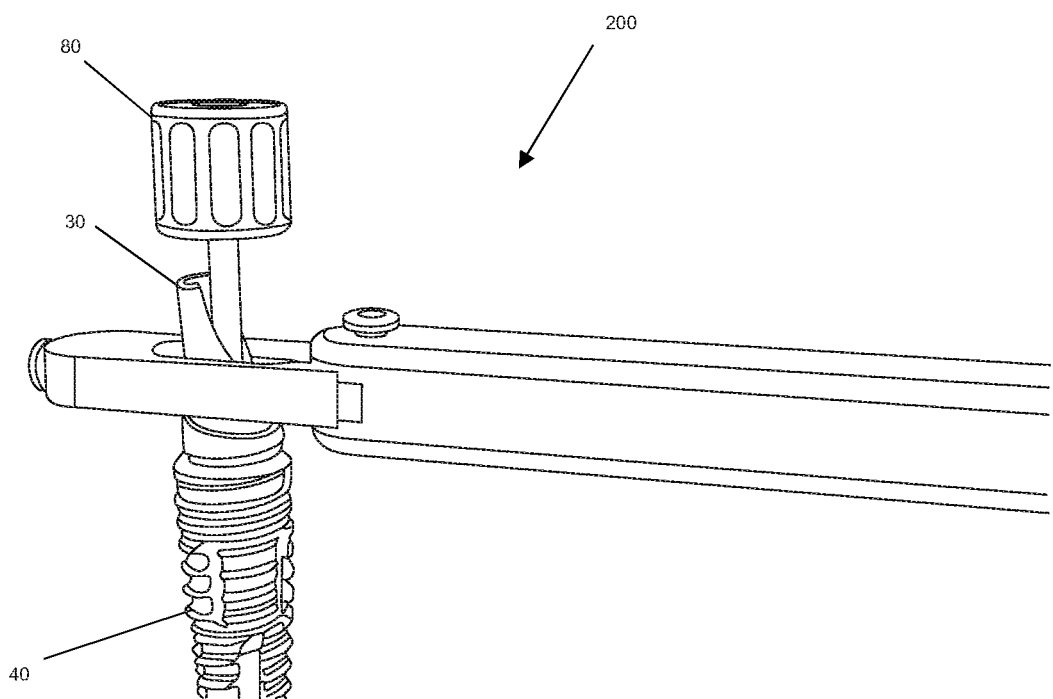
FIG. 12 is a perspective view of the present invention adjustably grasping an abutment for assistance in the driving of the screw into an implant.
Figure 13A:
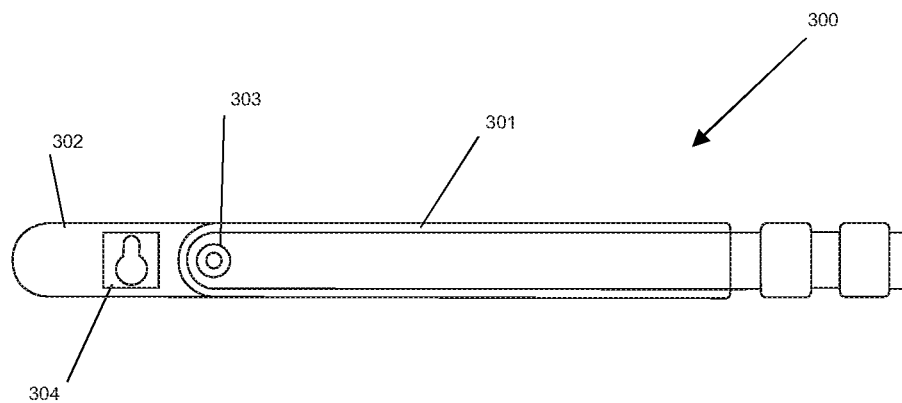
FIG. 13A is a front view of another embodiment of the present invention.
Figure 13B:
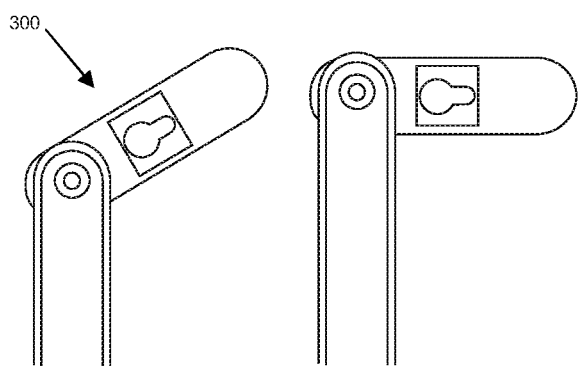
FIG. 13B is a front view of the head portion of another embodiment of the present invention.
Figure 14A:
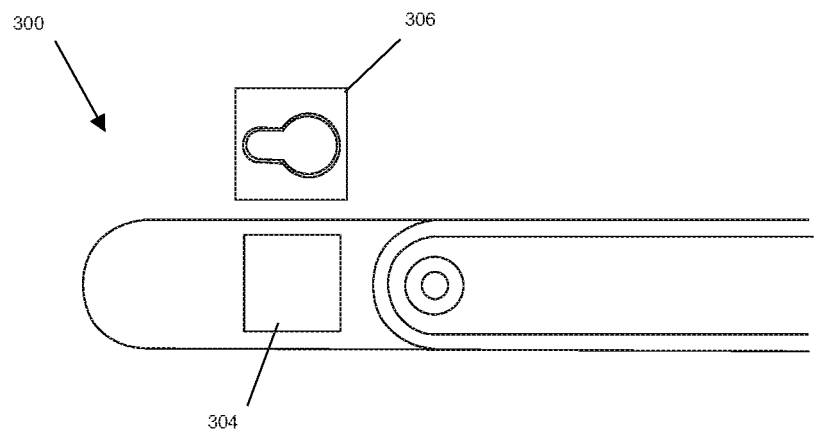
FIG. 14A shows the head portion of the present invention.
Figure 14B:
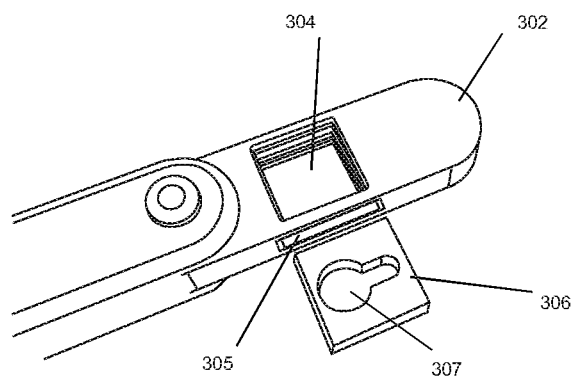
FIG. 14B is a perspective view of the head portion.
Figure 15A:
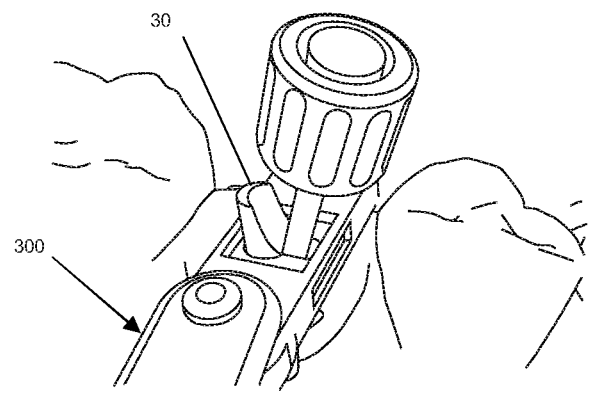
FIG. 15A is a perspective view of the present invention adjustably grasping an abutment for assistance in the driving of the screw into an implant.
Figure 15B:
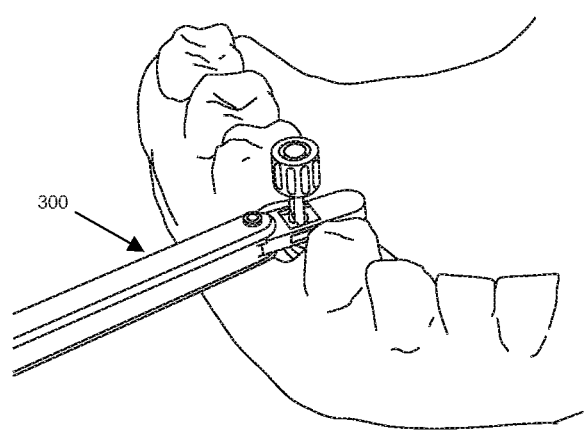
FIG. 15B is a perspective view of the present invention adjustably grasping an abutment for assistance in the driving of the screw into an implant.

In another embodiment of the present invention which is disclosed in FIGS. 10 to 12; the dental tool 200 comprises of a handle 201 pivotally connected to the head 202 from its proximal end at a pivot point via an adjusting screw 206. The head 202 of the dental tool 200 can be moved to the left and the right and be secured at each direction. It can be extended up to 90 degrees at each direction (180 range) which is one of the key features of this invention.

An oval-shaped central hole 203 is provided on the centre of the head portion 202 and provides a fastening mechanism to fix and lock the dental abutment in the central hole 203. A curved adjustable plate 204 is installed at the proximal end of the central hole 203, which is adjustable by a screw knob 205. The central bore 203 provides fractures on the inner side walls which facilitate the movement of the adjustable plate 204 inside the central hole 203. In operation, the abutment 30 is inserted into the central hole 203 and grasped and fixed by the curved adjustable plate into the hole 203 and being held within the hole 203. Once the abutment 30 is engaged within the dental tool 200 the dentist can transport the abutment 30 to the desired location within a patient mouth to affix the abutment 30 to an implant 40.

FIGS. 13A-13B, 14A-14B, 15A-15B show another embodiment of the dental tool 300 with a handle 301 that connects the head 302 via a hinge to the adjusting screw 303. The head 302 contains a square-shaped opening 304 and a slot 305 on the side of the head 302 which is used to insert and remove square plate 306. The square-plate 306 has a thickness of 3 mm and consists of a key-hole 307 in the centre with a divergency of 3 degrees on the walls to insert an abutment 30. The handle 301 is pivotally connected to the head 302 from the proximal end at the pivot point by a screw 303 so that the head can move 90-degrees to the right and left based on appropriate angle which is needed via insertion. Various interchangeable square plates 306 with different key-hole sizes and angles 307 can be used in this dental tool 300. The head 302 can be moved to the left and the right and be secured at each direction. It can be extended up to 90 degrees at each direction (180 range).

Figure 16:
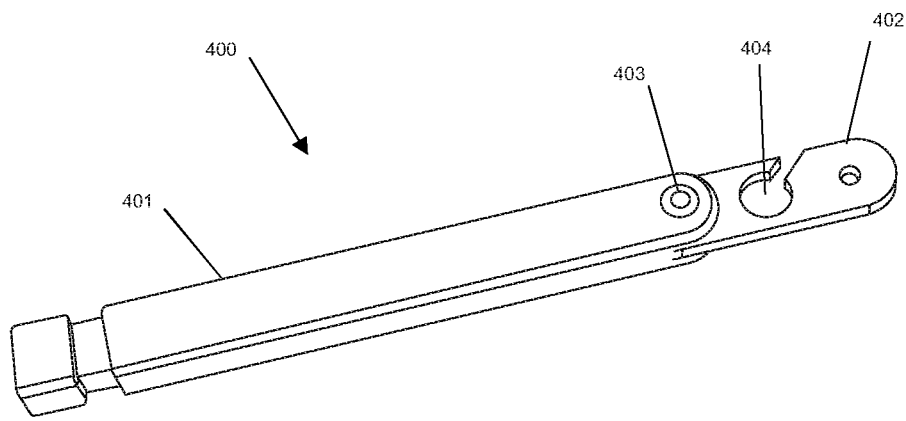
FIG. 16 is a perspective view of another embodiment of the present invention.
Figure 17:
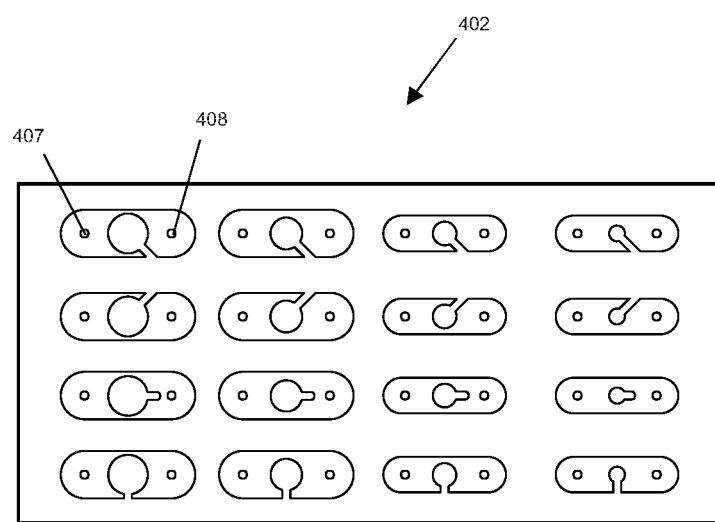
FIG. 17 shows various configurations of replaceable head portions according to FIG. 16.
Figure 18:
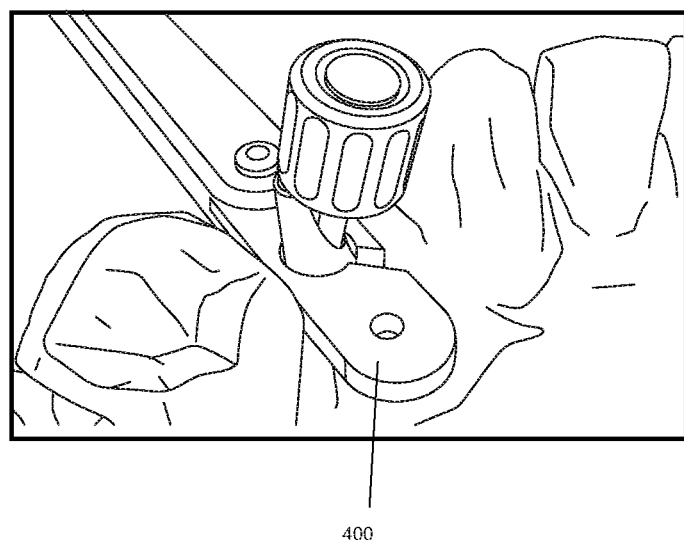
FIG. 18 is a perspective view of the present invention adjustably grasping an abutment for assistance in the driving of the screw into an implant.
Figure 19:
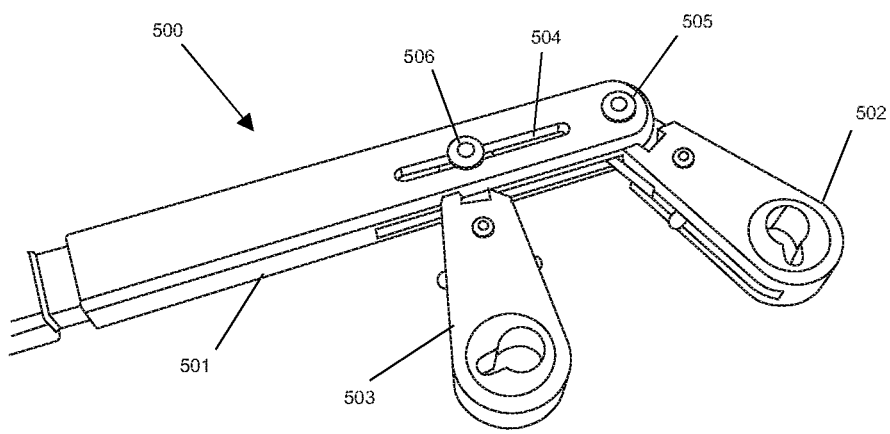
FIG. 19 is a perspective view of another embodiment of the present invention.
Figure 20:
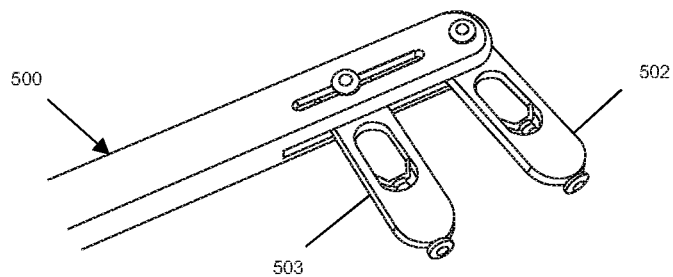
FIG. 20 shows the present invention with various head portions.
Figure 21:
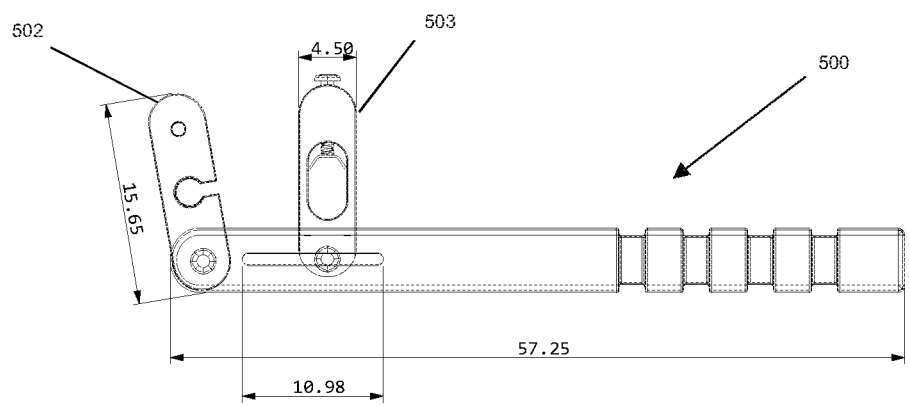
FIG. 21 shows the present invention with various head portion.
Figure 22:
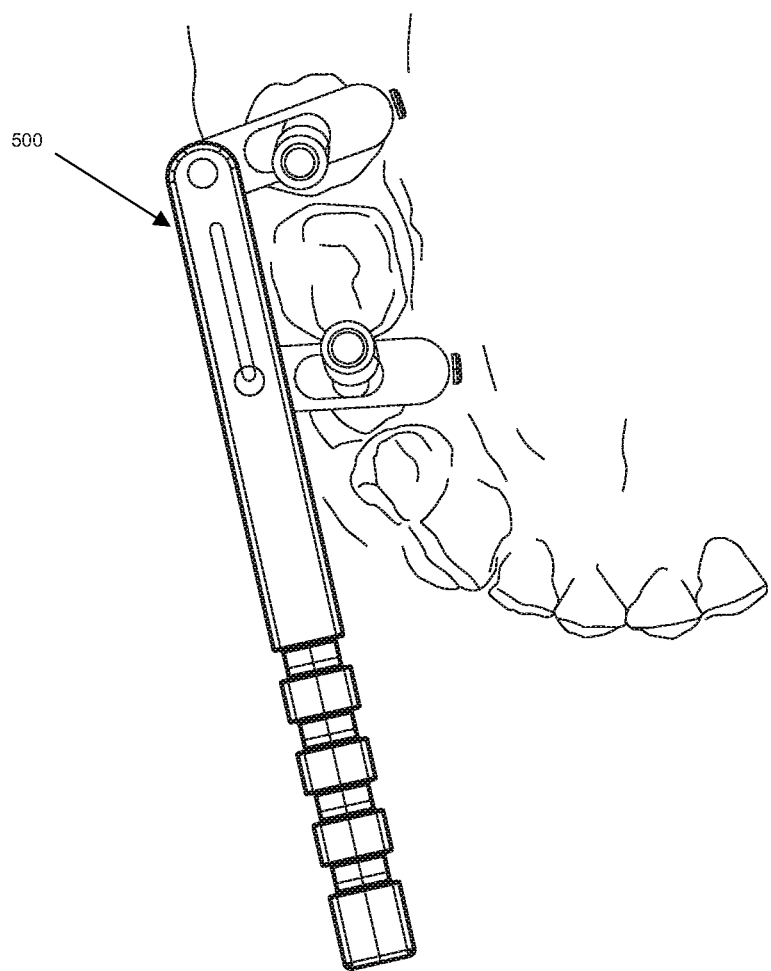
FIG. 22 is a perspective view of the present invention adjustably grasping two abutments for assistance in the driving of the screws into implants.
Figure 23A:
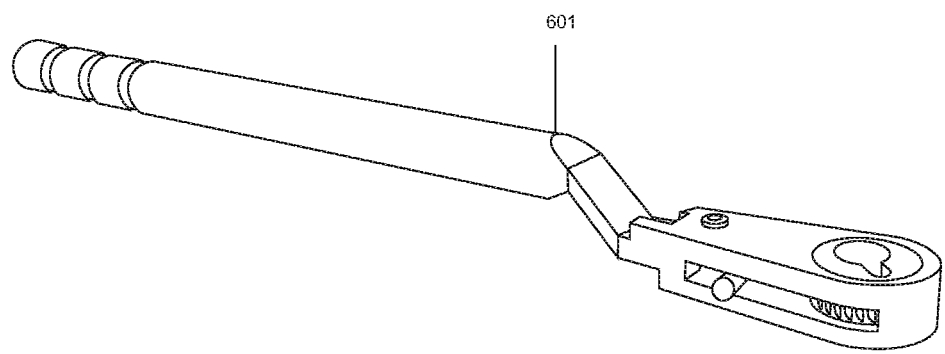
FIG. 23A is a perspective view of another embodiment of the present invention.
Figure 23B:
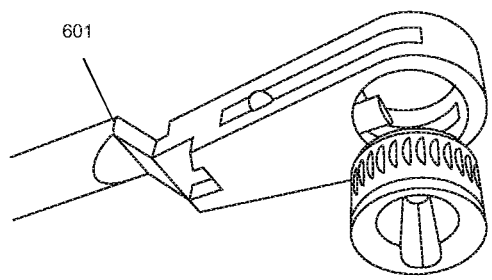
FIG. 23B is a perspective view of the head portion according to FIG. 23A.
Figure 23C:
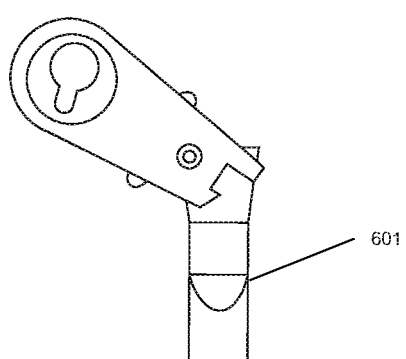
FIG. 23C is a perspective view of the head portion according to FIG. 23A.
Figure 26A:
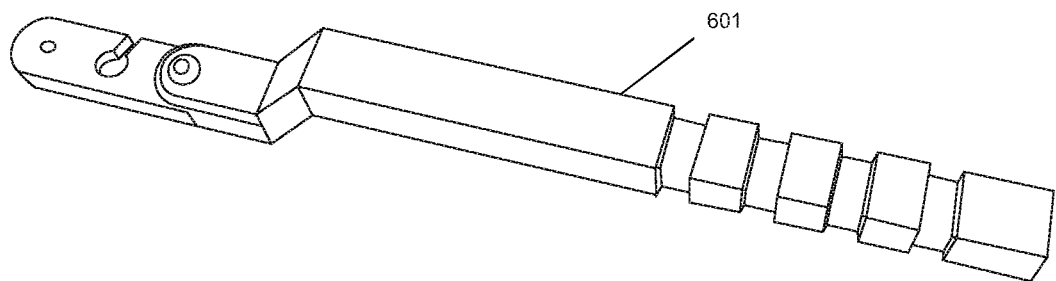
FIG. 26A is a perspective view of another embodiment of the present invention.
Figure 26B:
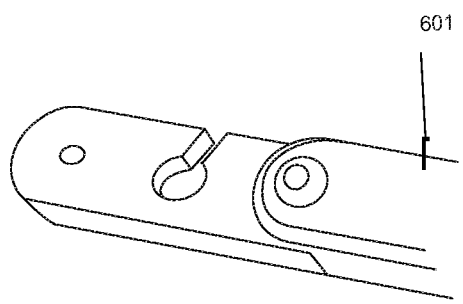
FIG. 26B is a perspective view of the head portion according to FIG. 26A.
Figure 26C:
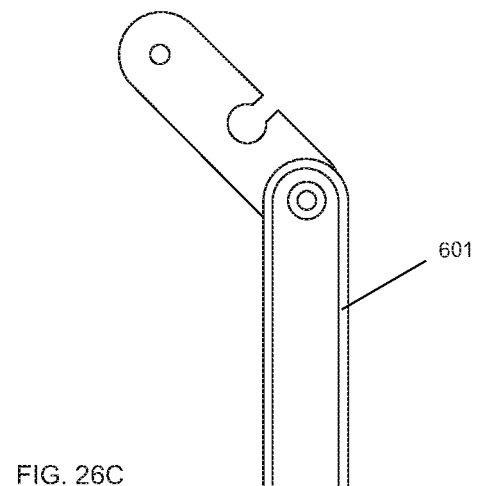
FIG. 26C is a perspective view of the head portion according to FIG. 26A.

According to FIGS. 16 to 18, the dental tool 400 has a handle 401 that connects by an adjusting screw 403 to the head 402. The head is a series of interchangeable solid plates with thickness of 3 mm, including a key-hole shape opening 404 which can be on various areas on the plates. The head 402 can be separated from the handle 401 and replaced with various shapes of heads by suitable connection techniques. There is a range of applicable shape and diameters for key-holes 404 on each plate in order to accommodate various sizes of abutments and implant parts. The main advantage and distinction of this embodiment is that the heads 402 can be attached to the handle, in both ends, at the top and at the bottom.

As shown in FIG. 17, each plate provides two connecting areas 407 and 408 to be connected to the handle. The keyhole walls display a divergency of 3 degrees. The head 402 can be moved to the left and the right and be secured at each direction. It can be extended up to 90 degrees at each direction (180 range).

According to FIGS. 19 to 22, in another embodiment, the present dental tool 500 consists of a handle 501 having two hinges on its proximal end to receive two heads, a first head 502 and a second head 503. The heads 502 and 503 are connected via hinges in a distance apart to two adjusting screws 504 and 505. The heads 502 and 503 have a length about 1-1.5 cm and a width about 4.5-6.5 mm and can be removed and replaced.

In operation the dental tool 500 can be used for installment of two abutments 30 and 32 at a time. The first head 502 is connected to the distal end of the handle 501 by an adjusting screw 504 on a first connection point and fixed thereon. The second head 503 is attached by a second adjusting screw 505 in a distance to the first head 502 on a second connection point. The second screw 505 can be slidably move in a slot 506 on the handle 501 to adjust the distance between the first head 502 and the second head 503. The range of the movement is about 10-15 mm. Various head portions can be used in this dental tool 500 to operate as one single unit. The heads of the dental tool 500 cannot be moved to the left and the right and be secured at each direction.

According to FIG. 23A to 26C, in another embodiment, the handle of the dental tool is not straight and can be connected to various head portions with an angle about 115 degrees 601. This helps the practitioner to find better access to the implant sites in some cases especially in posterior areas of the mouth. The angle of the head portion to the handle can be fixed such that it is configured to access a certain side of a patient's mouth. The head portion can be attachable to the handle through a hinge.

Figure 27:
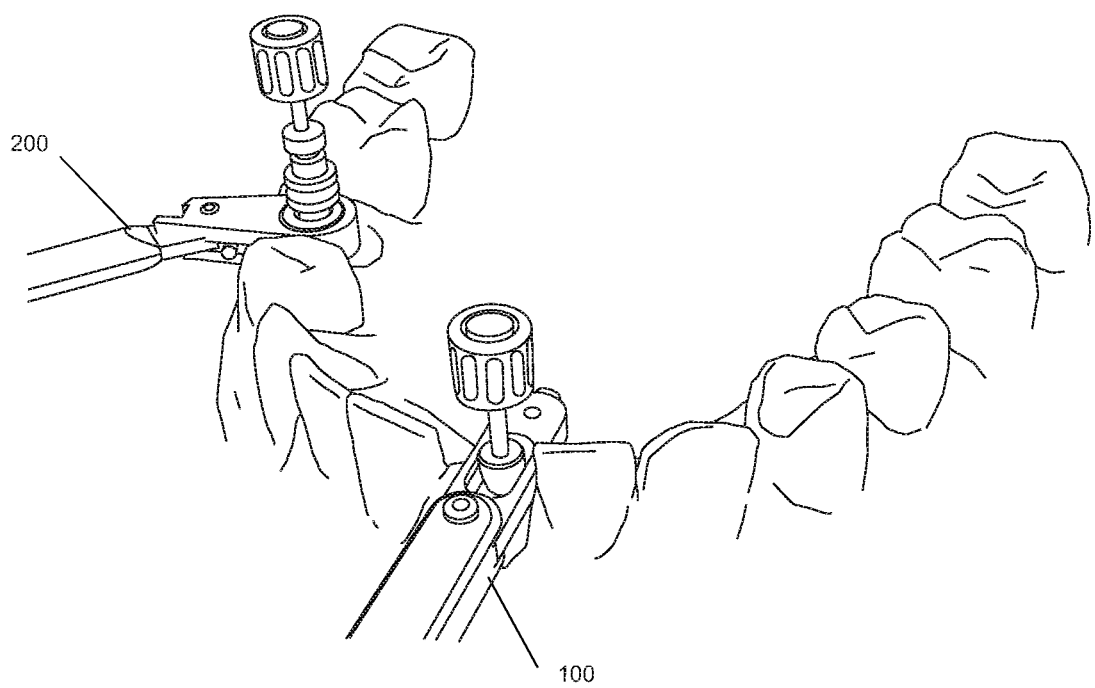
FIG. 27 is a perspective view of the present invention showing another application of the present invention.

The present dental tool in accordance with the present disclosure can be provided in "kit form." For example, a kit may comprise different type of heads a straight handle, an angled handle and a plurality of interchangeable heads. Additionally, or alternatively, the kit may comprise a plurality of replacement portions for the heads. As shown in FIG. 27, the practitioner can securely work on various implant sites with various embodiments of the dental 100 and 200.

Figure 28:
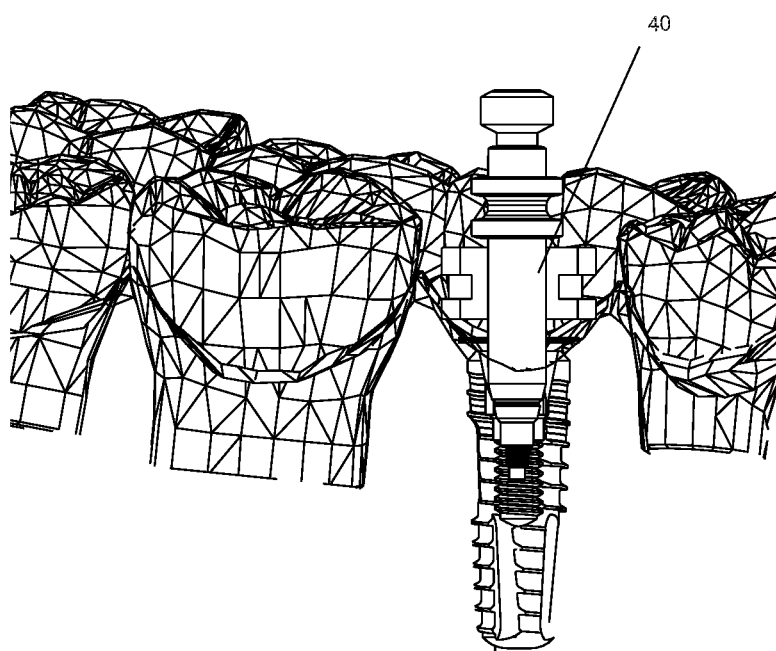
FIG. 28 is a perspective view of the implanted abutment positioned ready to mount replacement teeth.

FIG. 28 shows an implant 40 positioned into the patients jawbone by using the present invention ready to mount replacement teeth or a bridge into that area.

With respect to the above description, it is to be realized that the optimum relationships for the parts of the invention in regard to size, shape, form, materials, function and manner of operation, assembly and use are deemed readily apparent and obvious to those skilled in the art, and all equivalent relationships to those illustrated in the drawings and described in the specification are intended to be encompassed by the present invention.

What is claimed is:

1. A dental tool for installing a dental abutment, and impression coping, or a healing abutment, comprising:
    a) a head having a distal end and a proximal end for holding a dental abutment, an impression coping, or a healing abutment wherein said head comprising:
        i) an aperture at the distal end to receive a ratchet;
        ii) the ratchet has a keyhole-shaped aperture with an inner wall, wherein said keyhole-shaped aperture has a circular section and a stem section and wherein the inner wall convergences from an upper surface towards a lower surface of the ratchet to grasp and hold the dental abutment, and
        iii) a locking mechanism to fix and lock the ratchet in said aperture;
    b) an elongated handle pivotally and rigidly connected to said head from the proximal end at a pivot point and wherein said head moves 90 degrees to a right side or a left side;
        whereby the dental tool provides a secure access for a screw to an implant-driver tip for any abutment-body angulation and position.

2. The dental tool of claim 1, wherein the inner wall has 3°-degree convergences.

3. The dental tool of claim 1, wherein the locking mechanism comprises of a knob slidably movable by a lever in communication with a plurality of grip retaining gaps extended continuously around an outer side wall of the ratchet to rotatably and firmly grasp the ratchet.

4. The dental tool of claim 1, wherein the elongated handle is selected from the groups consisting of a straight body, a curved body or a combination of straight body and curved body.

5. The dental tool of claim 1, wherein the elongated handle has a length in the range of about 5 cm to about 7 cm.

6. The dental tool of claim 1, wherein said dental tool or said head are replaceable.

7. The dental tool of claim 1, wherein the dental tool is made of medical titanium alloy or stainless steel.

8. The dental tool of claim 1, wherein said dental tool further has a pair of heads, a first-head and a second-head.

9. The dental tool of claim 8, further the elongated handle has a first connection point and a second connection point, which the first-head connected to the first connection point, and the second-head connected to the second connection point, and the second-head is in a predefined distance to the first-head for installing two dental abutments at a time.

10. The dental tool of claim 8, wherein the elongated handle further has a slot which the second-head is slidably moveable in the slot.

\* \* \* \* \*